Figure 1:
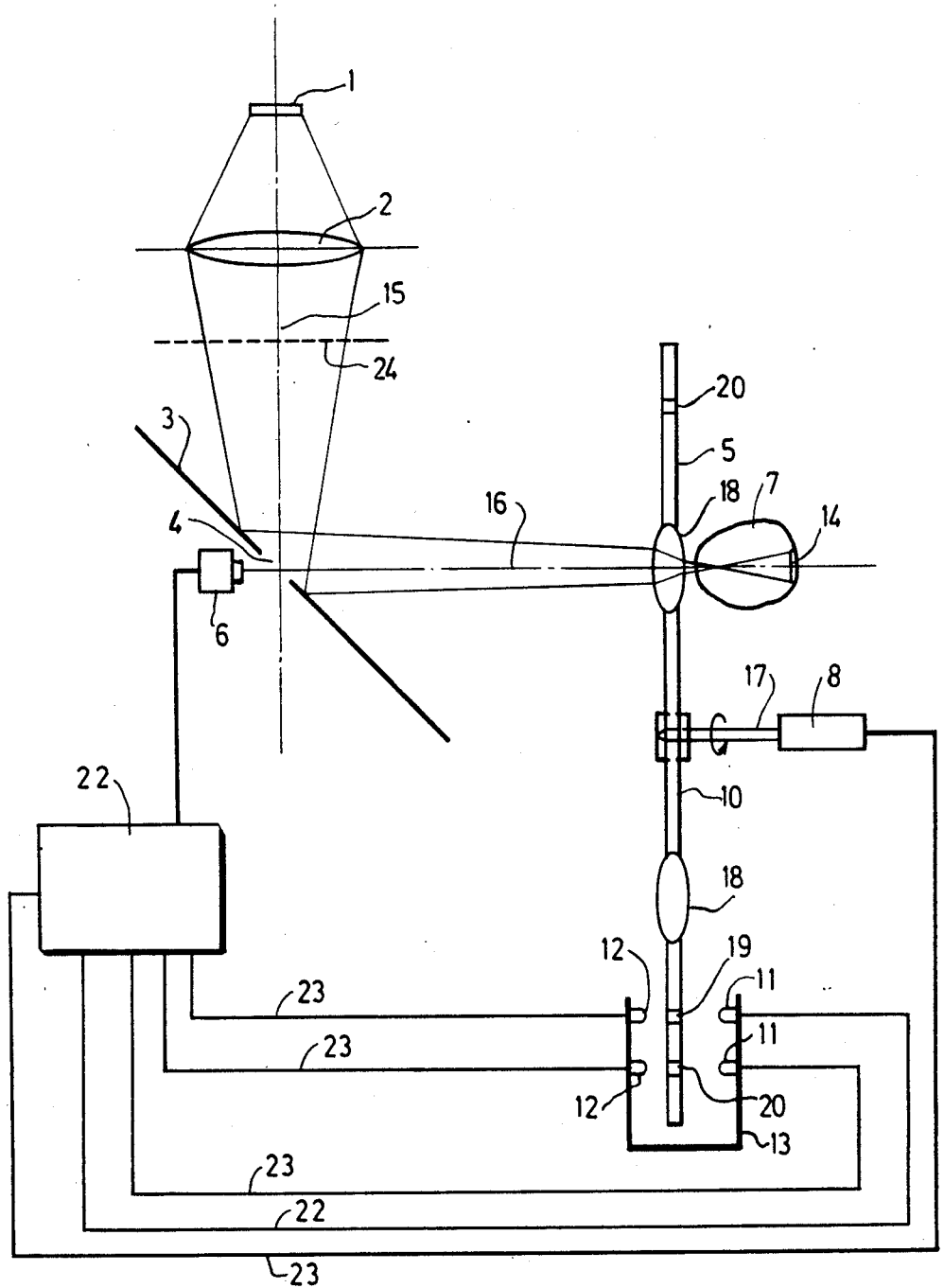

United States Patent [19]

Hache et al.

[11] Patent Number: 4,673,265

[45] Date of Patent: Jun. 16, 1987

[54] PROCEDURE AND DEVICE FOR AUTOMATIC REFRACTOMETRIC MEASUREMENT OF THE DEGREE OF AMETROPIA OF A HUMAN EYE

[75] Inventors: Jean C. Hache, Lille; Mireille Servant, Villeneuve D'Ascq, both of France

[73] Assignee: Essilor International (Compagnie Generale d'Optique), Creteil, France

[21] Appl. No.: 904,777

[22] Filed: Sep. 5, 1986

Related U.S. Application Data

[63] Continuation of Ser. No. 769,758, Aug. 26, 1985, abandoned, which is a continuation of Ser. No. 442,588, Nov. 18, 1982, abandoned.

[30] Foreign Application Priority Data

Nov. 23, 1981 [FR] France ............................... 81 21868

[51] Int. Cl.⁴ .............................................. A61B 3/10
[52] U.S. Cl. .................................... 351/217; 351/205; 351/211
[58] Field of Search ............... 351/205, 210, 211, 212, 351/213, 216, 217

[56] References Cited

U.S. PATENT DOCUMENTS 3,791,719  2/1974  Kratzer et al. ...................... 351/217

Primary Examiner—Rodney B. Bovernick
Assistant Examiner—P. M. Dzierzynski
Attorney, Agent, or Firm—Burgess, Ryan & Wayne

[57] ABSTRACT

This invention concerns a procedure and device for refractometric measurement of the degree of ametropia of a human eye.

The device for this invention comprises a light-emitting source combined with a focusing lens, which produces an image of this source on the retina of the eye to be tested, a succession of test lenses which are placed in turn between the eye and the focussing lens, so that the optical axis of the relevant test lens coincides with the optical axis of the eye, and a light-intensity detector placed on this same axis at a fixed distance from the eye, together with means of identifying which test lens causes the detector to emit a signal of minimum intensity.

The invention applies to instruments to measure visual acuity, more specifically in handicapped or very young patients.

3 Claims, 2 Drawing Figures

PROCEDURE AND DEVICE FOR AUTOMATIC REFRACTOMETRIC MEASUREMENT OF THE DEGREE OF AMETROPIA OF A HUMAN EYE

This application is a continuation of application Ser. No. 769,758, filed Aug. 26, 1985, now abandoned, which application is a continuation of application Ser. No. 442,588, filed Nov. 18, 1982, now abandoned.

This invention concerns a procedure and device for automatic refractometric measurement of the degree of ocular ametropia, more specifically of the human eye.

Existing procedures and devices of this type require quite a long time for each of the measurements needed to assess the degree of ametropia of the eye being examined, in order to be able to select the right corrective spectacle lens. In addition, existing devices are rather cumbersome and complicated, making them difficult to transport, so that the patient has to remain in a predetermined position throughout the testing procedure; this usually involves a sitting position, which means that such procedures and devices cannot be used with certain types of patients, or only with great difficulty. Such patients include those who cannot remain seated for long periods, because of their age and/or physical condition, even though this position is obligatory for the implementation of conventional refractometric methods, because of the design of the installations involved. Neither are such procedures and devices suitable for use with patients who are unable to keep their eye steady and open, without blinking, long enough for each of the many measurements, normally involving a period of about ten seconds. This applies in particular to very young children and hyperexcitable patients, and in general to any patients who, for whatever reason, cannot stand the glare of the light needed for refractometric measurements.

The purpose of this invention is to provide a procedure and device that will overcome the drawbacks of existing methods and equipment, making it possible to test a patient's eye in any position of the body, and regardless of the patient's sensitivity to glare. The device for this invention allows tests to be performed, whether the patient is seated, standing, lying or, in the case of infants, held in another person's arms. It also allows each refractometric measurement to be taken automatically, in a very short period—more specifically, for very young or hyperexcitable patients, in the time elapsing between two blinks, caused by uncontrollable reflexes.

In the process according to this invention, making it possible to achieve this result, and on which the device for this invention is based, light rays from a light source are made to pass through a focusing lens possessing predetermined optical properties, on to the retina of the eye being tested, a light intensity detector being used to detect, on a fixed plane, the rays emitted by the image produced on the retina, the light source and detector being offset in relation to each other, a succession of test lenses possessing different optical properties is placed in turn between the eye on the one hand, and the focusing lens and detector on the other, and lens which, when thus interposed, causes the punctum remotum of the eye to coincide most closely with the said fixed plane, thereby reducing the detector signal to minimum intensity.

Clearly, if the properties of the focusing lens and test lens thus identified are known, and with predetermined distances between such lenses and the eye, and between the eye and the aforementioned fixed plane, a reference value can be obtained for the distance between the retina and the punctum remotum, providing, as known in the prior art, measurement of the degree of ametropia of the eye being thus tested, thereby enabling the right corrective lens to be prescribed.

The novel device used to perform the procedure described above comprises a light source combined with a focusing lens which produces an image of this source on the retina of the eye, a succession of testing lenses, which are placed in turn between the eye and the focusing lens, in such a way that the optical axis of the relevant lens coincides with the optical axis of the eye, and a light-intensity detector positioned on this same axis at a fixed distance from the eye, and further comprises means of identifying which lens reduces the detector signal to minimum intensity.

The device described above can be constructed in a very compact form, weighing relatively little, and making it extremely easy to handle, so that it can be placed easily in any convenient position for accurate refractometric examination to suit the patient, unlike known devices, which require the patient to remain in a certain position (usually seated), to suit the position and orientation of the testing apparatus.

Furthermore, the device according to this invention records each measurement, as a test lens passes in front of the eye, more or less instantaneously, so that blinking by a hypersensitive or hyperexcitable patient has very little effect on the test, except on the very rare occasions when passage of a lens and blinking of the eye coincide, in which case the test can easily be repeated with minimum loss of time, and with the likelihood that simultaneous passage of the lens and blinking of the eye will not recur. In any case, it is no longer necessary, when using the device for this invention, to try and force the patient to abstain from blinking during a given period of time, usually quite long, as is the case when devices in the prior art are used.

Figure 2:
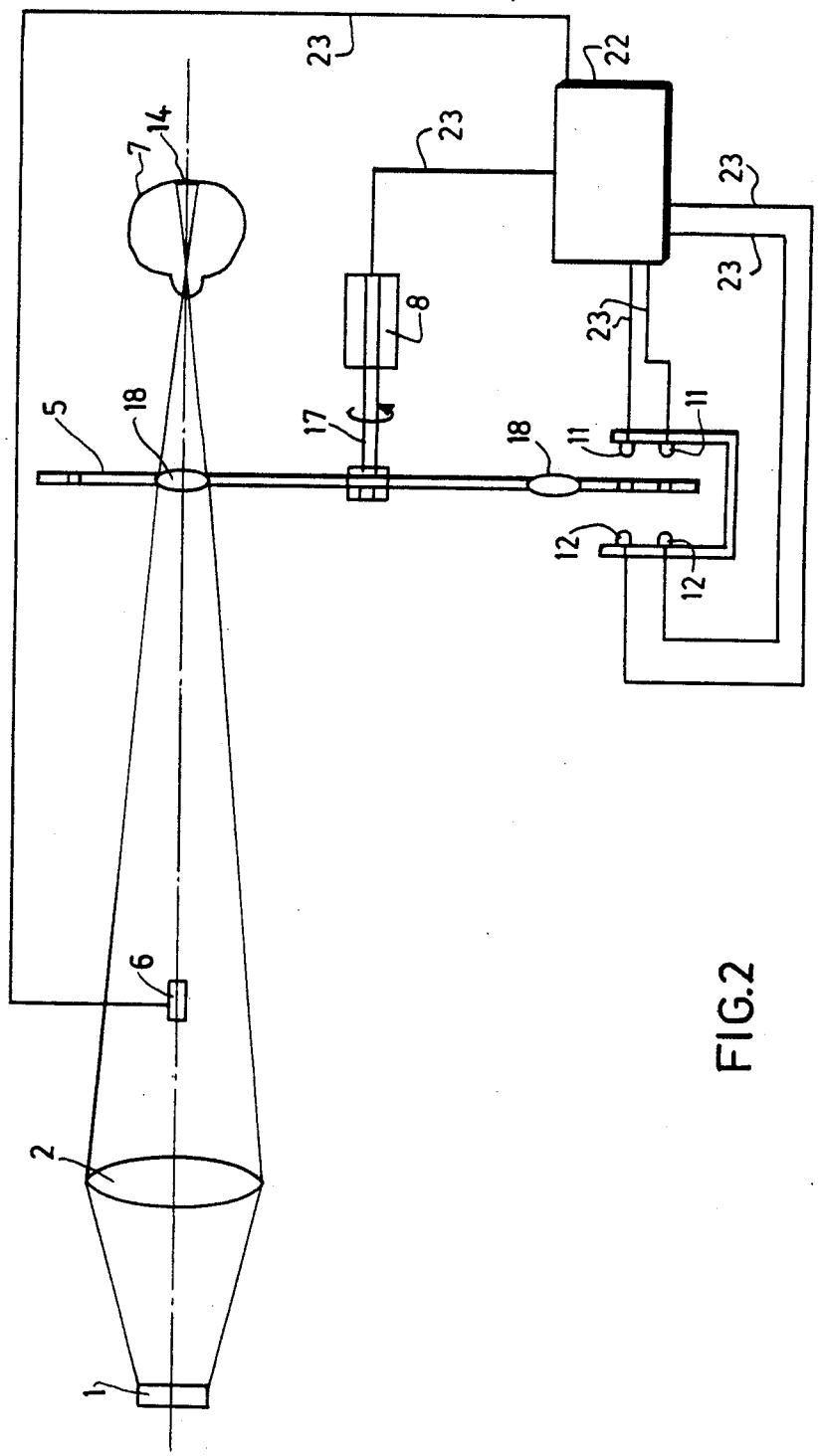

Further details of the invention will emerge from the following detailed description of possible enbodiments, with reference to the accompanying figures:

FIG. 1 showing one embodiment of the device for this invention;

FIG. 2 showing another embodiment of this device.

The device shown in FIG. 1 comprises a light source 1, which may be linear, circular, annular, or comprise one or more light-emitting components that can be moved anglewise around a geometrical centre point, this fourth version being particularly useful when employing the device on patients suffering from astigmatism. The light source 1 is slightly off the axis of the focusing lens 2, being formed here of a ring, only the circumferential portion of which emits light.

Opposite this light source 1 is a convex focusing lens 2, which, by means of a mirror 3, produces an image 14 on the retina of the patient's eye 7. This mirror 3 is tilted at an angle of 45° to the optical axis 15 of the lens 2 concentric with the source 1, and also to the optical axis 16 of the eye 7. The mirror also contains a small elliptical hole 4, so designed that its projection on a plane at right angles to the optical axis 16 of the eye is circular. A light detector 6 is placed behind the mirror 3, aligned with the optical axis 16, which passes through the centre of the hole 4. This detector receives light rays emitted by the image 14 formed on the retina, and measures their intensity.

A motor 8 and shaft 17 cause a circular disc 5 to revolve. This disc contains a number of test lenses 18, equidistant anglewise, and the centers of which are situated on a circle concentric with the geometrical axis of the shaft 17. Each test lens 18 is of different optical power from adjoining lenses, the difference between any two consecutive lenses being preferably 1 diopter.

The disc 5 contains a single synchronization hole 19 located on a larger circle than that formed by the centers of the test lenses 18. Each such lens 18 is also accompanied by a hole 20, the center of each such hole being located on the same radius as the center of the corresponding lens 18. A fixed bracket 13, encompassing part of the disc 5, carries two photodiodes 11 on one side, and two phototransistors 12 on the other side, each opposite one of the photodiodes. These diodes 11 and transistors 12 are placed in such a way that when the disc 5 rotates, the synchronization hole 19 passes between one diode and its accompanying transistor, while the holes 20 pass between the other diode and its accompanying transistor, the geometrical axis of each such hole coinciding, as it passes between the diode and transistor, with their common axis. The motor 8, diodes 11 and transistors 12 are connected electrically by conductors 23 with an electronic synchronization control device 22.

This control device 22 also identifies and indicates which test lens 18 possesses the right optical power so that the punctum remotum (corresponding to the eye's maximum accomodation distance) is situated on the optical plane of the light detector 6, which thereupon detects and displays minimum light intensity (ideally, zero intensity). The ophthalmologist or optometrist can then calculate the properties of the corrective lens to be prescribed, on the basis of the characteristics of the lenses 2 and 18, the distances separating these two lenses from each other and from the eye, and the distance between the eye and the detector 6.

The simplified embodiment illustrated in FIG. 2 does not comprise any mirror, and the light source 1, focusing lens 2 and test lenses 18 on the disc 5 are aligned directly with the eye 7, while the detector 6 is positioned between the lens 2 and disc 5. This device otherwise contains the same components as the device in FIG. 1, identical or similar items bearing the same references in both figures.

FIG. 1 shows an optical filter 24, for example a red filter, which can be placed below the focusing lens 2.

It is clear that such a device, designed to perform the new measuring procedure described above, can be constructed in a very compact, light weight form, so that it can be placed in the most convenient position for the patient, unlike the rather complicated devices in the prior art, which are cumbersome and heavy, and require the patient to remain in a fixed position (usually seated) in relation to the appliance. Refractometric measurements can also be taken very quickly and automatically, so that it is no longer necessary to force the patient to keep his eye open and fixed for an extended period, as is the case with devices in the prior art.

The light source is preferably offset slightly from the optical axes of the device and the eye; in another embodiment, the detector 6 is offset in relation to the optical axes of the light source and eye and to the general axis of the device (for the purposes of this description and the claims stated below, "offset" is taken to signify that the component in question, whether light source or detector, comprises no active part situated on the relevant axis).

The light source may emit a pinpoint or filiform light, or may comprise two diametrically opposite light components. It may also comprise one lighting component which is off-centered and which can be moved anglewise round the center of the source, making it easier to examine the visual acuity of an astigmatic patient.

The invention is in no way confined to the embodiments described and illustrated here, many variants will be possible for someone skilled in the art, without any departure from the spirit of the invention. For example, the succession of test lenses mentioned in this description and in the claims below may be replaced by a variable-focus device.

What is claimed is:

1. Apparatus for refractometrically measuring the degree of ametropia of a human eye placed at a location predetermined with respect to said apparatus, comprising:

(a) a light source;

(b) optical means for shaping light emitted by said light source into a focused light beam propagated along a light path;

(c) a mirror interposed in said light path between said source and said eye for directing said beam to said eye in a given direction defined by an optical test axis coinciding with the optical axis of said eye, so as to produce on the retina of said eye an image of said light source, said mirror including an aperture substantially centered in said light path such that a light projection on a plane at right angles to the optical axis of the eye is circular;

(d) a circular disk mounted for rotation about its center;

(e) a plurality of corrective testing lenses mounted on said circular disk with respective centers of said lenses located on a common circle having its center coinciding with the center of said disk, each lens being positionable adjacent said eye in said reflected light path from said mirror, and said testing lenses having different respective optical power values;

(f) motor means for rotating said disk stepwise about an axis of rotation which contains the center of said disk and which is parallel to said optical test axis;

(g) indicia means for identifying each of said testing lenses and for indicating when any one of the thus identified testing lenses is interposed across said reflected light path, said indicia means including optically detectable holes in said disk and photo detector means for optically detecting said holes in said disk to indicate when a testing lens is interposed across said reflected light path;

(h) a light detector means disposed and optically centered on the optical test axis behind the mirror for receiving light reflected through the interposed test lens and through the aperture in the mirror; and (i) signal generating and processing means associated with said respective corrective testing lens and said light detector means for identifying that one of said corrective testing lenses which, when interposed across said light beam, transmits to said light detector means a minimum amount of light reflected by said retina in response to said image.

2. The apparatus according to claim 1 wherein said photo-detector means are located on said apparatus in close proximity to said indicia means.

3. A method of refractometrically measuring the degree of ametropia of a human eye placed at a predetermined location, comprising the steps of:
 (a) shaping light emitted by a light source into a focused light beam propagated along a light path;
 (b) directing said beam to said eye in a given direction defined by an optical test axis coinciding with the optical axis of said eye so as to produce on the retina of said eye an image of said light source, by interposing a mirror in said light source between said source and said eye, with an aperture of said mirror being substantially centered in said light path such that a light projection on a plane at right angles to the optical axis of the eye is circular;
 (c) reflecting said image produced on said retina through one of a plurality of corrective testing lenses mounted on a rotatable circular disk about a common circle with each lens being positionable adjacent said eye in said reflected light path from said mirror and having different respective optical power values;
 (d) rotating said disk stepwise about an axis of rotation which contains the center of said disk and which is parallel to said optical test axis;
 (e) identifying each of said testing lenses interposed in said reflected light path;
 (f) indicating when any one of the thus identified testing lenses is interposed across said reflected light path by means of optically detectable holes in said disk and photo detector means for optically detecting the holes in the disk;
 (g) disposing light detector means, optically centered on the optical test axis behind the mirror, for receiving light reflected through the interposed test lens and through the aperture in the mirror; and
 (h) identifying that one of said corrective testing lenses which, when interposed across said light beam, transmits a minimum amount of light reflected by said retina to said light detector means, in response to said image.

* * * * *